US012121724B2

(12) United States Patent
Young et al.

(10) Patent No.: US 12,121,724 B2
(45) Date of Patent: Oct. 22, 2024

(54) SYSTEMS AND METHODS FOR FACILITATING OPTIMAL ALIGNMENT OF COCHLEAR IMPLANT SYSTEM COMPONENTS

(71) Applicant: Advanced Bionics AG, Staefa (CH)

(72) Inventors: Maosong Young, Tujunga, CA (US); Roger S. Meier, Canyon Country, CA (US)

(73) Assignee: Advanced Bionics AG, Staefa (CH)

( * ) Notice: Subject to any disclaimer, the term of this patent is extended or adjusted under 35 U.S.C. 154(b) by 489 days.

(21) Appl. No.: 16/640,466

(22) PCT Filed: Aug. 24, 2018

(86) PCT No.: PCT/US2018/048027
§ 371 (c)(1),
(2) Date: Feb. 20, 2020

(87) PCT Pub. No.: WO2019/046133
PCT Pub. Date: Mar. 7, 2019

(65) Prior Publication Data
US 2020/0215328 A1 Jul. 9, 2020

Related U.S. Application Data

(63) Continuation-in-part of application No. PCT/US2017/048974, filed on Aug. 28, 2017.

(51) Int. Cl.
*A61N 1/05* (2006.01)
*A61N 1/36* (2006.01)
(Continued)

(52) U.S. Cl.
CPC ....... *A61N 1/36039* (2017.08); *A61N 1/0541* (2013.01); *A61N 1/37247* (2013.01);
(Continued)

(58) Field of Classification Search
None
See application file for complete search history.

(56) References Cited

U.S. PATENT DOCUMENTS

| | | | |
|---|---|---|---|
| 6,073,050 A | 6/2000 | Griffith | |
| 6,752,155 B2 | 6/2004 | Behm | |

(Continued)

FOREIGN PATENT DOCUMENTS

| | | |
|---|---|---|
| CN | 104582786 | 4/2015 |
| EP | 2279025 | 2/2011 |

(Continued)

OTHER PUBLICATIONS

International Search Report and Written Opinion received in International Application No. PCT/US17/048974, dated May 4, 2018.

(Continued)

*Primary Examiner* — Erica S Lee
(74) *Attorney, Agent, or Firm* — ALG Intellectual Property, LLC

(57) ABSTRACT

An exemplary cochlear implant alignment system includes a cochlear implant system and a component alignment presentation system. The cochlear implant system includes an electrode lead and a cochlear implant that generates a wireless back telemetry signal during an insertion procedure of the electrode lead into a cochlea of a receipt. The cochlear implant system also includes an external headpiece configured to detect the wireless back telemetry signal generated by the cochlear implant and a sound processor configured to generate a Received Signal Strength Indicator (RSSI) signal based on a signal strength of the detected wireless back telemetry signal. The component alignment presentation system includes a processing device configured to receive the RSSI signal from the sound processor and to present an indication of a degree of alignment of the headpiece with the (Continued)

cochlear implant to assist a user in 15 aligning the headpiece with the cochlear implant during the insertion procedure.

15 Claims, 8 Drawing Sheets

(51) Int. Cl.
*A61N 1/372* (2006.01)
*H02J 50/10* (2016.01)
*H02J 50/80* (2016.01)
*H02J 50/90* (2016.01)

(52) U.S. Cl.
CPC .............. *H02J 50/10* (2016.02); *H02J 50/80* (2016.02); *H02J 50/90* (2016.02); *H04R 2225/41* (2013.01); *H04R 2225/55* (2013.01)

(56) References Cited

U.S. PATENT DOCUMENTS

| | | | |
|---|---|---|---|
| 7,009,362 B2 | 3/2006 | Tsukamoto et al. | |
| 7,486,048 B2 | 2/2009 | Tsukamoto et al. | |
| 7,699,060 B2 | 4/2010 | Behm | |
| 7,774,069 B2 | 8/2010 | Olson et al. | |
| 8,140,161 B2 | 3/2012 | Willerton et al. | |
| 8,321,027 B2 | 11/2012 | Mozzi et al. | |
| 9,031,666 B2 | 5/2015 | Fell | |
| 9,042,985 B2 | 5/2015 | Marsh et al. | |
| 9,205,269 B2 | 12/2015 | Marsh et al. | |
| 9,375,567 B2 | 6/2016 | Fell | |
| 9,452,296 B2 | 9/2016 | Forsell | |
| 2003/0025612 A1* | 2/2003 | Holmes | H04Q 9/02 340/870.02 |
| 2007/0260293 A1* | 11/2007 | Carpenter | A61N 1/3727 607/59 |
| 2010/0217353 A1 | 8/2010 | Forsell | |
| 2013/0211479 A1* | 8/2013 | Olson | A61N 1/3787 607/61 |
| 2014/0088665 A1* | 3/2014 | Marsh | A61N 1/37252 607/54 |
| 2015/0127069 A1* | 5/2015 | Dearden | A61N 1/3787 320/108 |
| 2016/0165360 A1* | 6/2016 | Kulkami | H04R 3/005 381/60 |
| 2016/0331964 A1* | 11/2016 | Xiao | A61N 1/37247 |
| 2016/0345830 A1 | 12/2016 | Raisoni et al. | |
| 2017/0080240 A1 | 3/2017 | Peter | |
| 2017/0161449 A1 | 6/2017 | Meskens | |
| 2017/0235332 A1* | 8/2017 | von Badinski | G02B 19/0052 361/679.03 |
| 2018/0056058 A1* | 3/2018 | Heasman | A61N 1/36036 |
| 2018/0010333 A1 | 4/2018 | Balslev | |

FOREIGN PATENT DOCUMENTS

| | | |
|---|---|---|
| EP | 2388043 | 11/2011 |
| EP | 1904153 | 4/2015 |
| EP | 1867362 | 4/2016 |
| WO | 2009051539 | 4/2009 |
| WO | 2014052900 | 4/2014 |
| WO | 2016109324 | 7/2016 |
| WO | 2016191715 | 12/2016 |

OTHER PUBLICATIONS

International Search Report and Written Opinion received in International Application No. PCT/US18/048027, dated Oct. 29, 2018.

* cited by examiner

SYSTEMS AND METHODS FOR FACILITATING OPTIMAL ALIGNMENT OF COCHLEAR IMPLANT SYSTEM COMPONENTS

RELATED APPLICATIONS

The present application claims priority to PCT International Application No. PCT/US17/48974, filed Aug. 28, 2017, the contents of which are hereby incorporated by reference in their entirety.

BACKGROUND INFORMATION

Cochlear implant systems are used to provide, restore, and/or improve hearing loss suffered by cochlear implant recipients who use the cochlear implant systems. In operation, typical cochlear implant systems include one or more internal components implanted within the recipient (e.g., including a cochlear implant that applies electrical stimulation to the recipient by way of a permanently affixed electrode lead that is inserted into the recipient's cochlea), as well as one or more external components operating external to the recipient (e.g., including a sound processor, a headpiece, etc.). In order for external and internal components to properly interoperate, communication between the external and internal components is commonly carried over a transcutaneous wireless link. For example, an external sound processor may transmit operating power and/or data (e.g., stimulation parameters) to an internal cochlear implant by way of an external headpiece that is aligned on the head with the cochlear implant and includes a communication component (e.g., an antenna coil or the like) for transmitting the power and data through the skin to the cochlear implant.

In some examples, a person may align external and internal components of the cochlear implant system using visual verification or other facilitators such as magnets attached to the external and/or internal cochlear implant system components. In certain circumstances, however, such visual verification, as well as magnetic and other such alignment facilitators, may not be available, or may be relatively ineffective. As such, it may be difficult and/or inconvenient in such circumstances to align external and internal cochlear implant system components. For example, during certain surgical procedures on the recipient's head, various obstructions (e.g., bandages, surgical drapes and coverings, etc.) may obstruct a surgeon's view of the recipient's head and may also blunt a magnetic attraction between the external and internal components.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
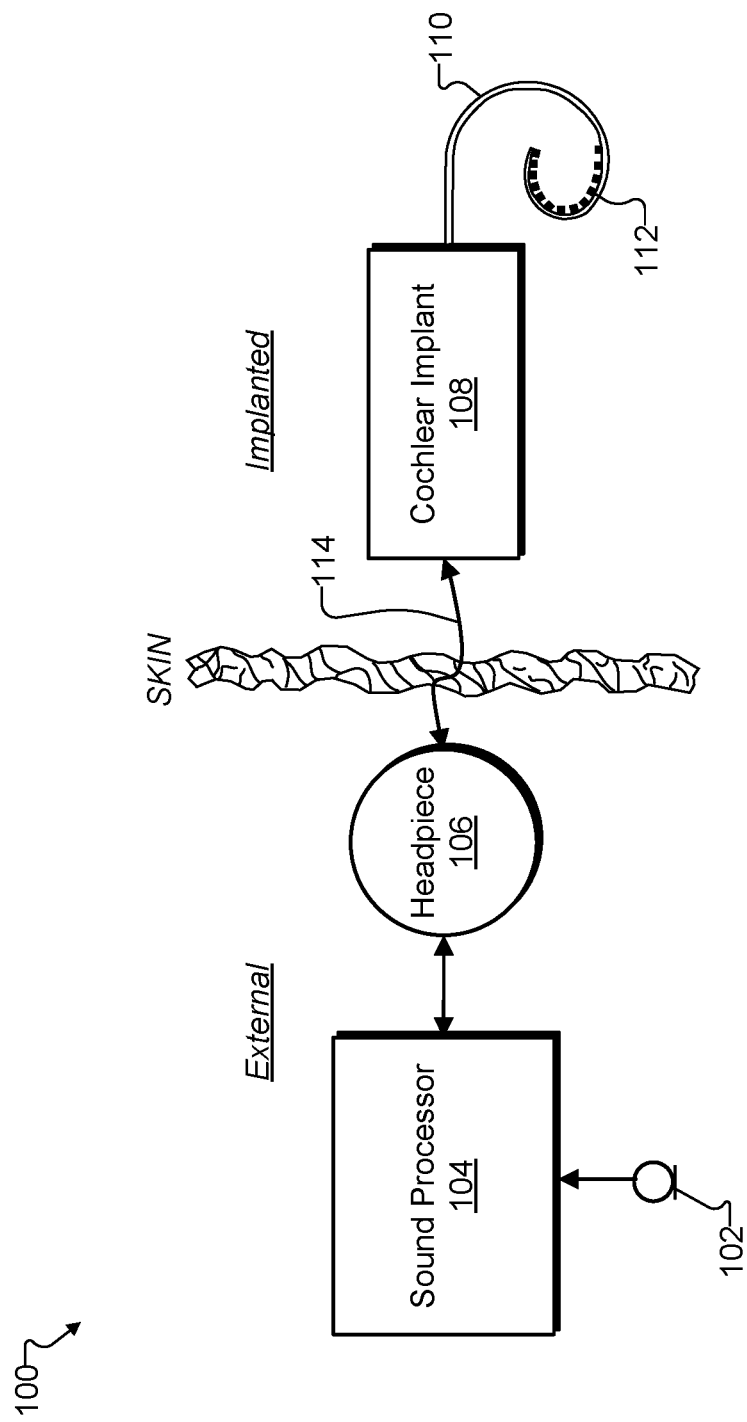
FIG. 1 illustrates an exemplary cochlear implant system according to principles described herein.

Systems and methods for facilitating alignment of cochlear implant system components are described herein. In particular, the systems and methods described herein may assist users in achieving a higher degree of alignment than may be conveniently achieved without use of the systems and methods. For example, an external component such as a headpiece and an internal component such as a cochlear implant may be aligned to a relatively high degree when a communication component included within the headpiece (e.g., an antenna coil or the like) is positioned so as to be disposed directly over a corresponding communication component included within the cochlear implant. In contrast, the headpiece and the cochlear implant may be aligned to a lesser degree when the communication components are near one another, but are offset to some extent from a most optimal position. As mentioned above, alignment of cochlear implant system components to a relatively low degree may be particularly problematic during surgical operations such as an insertion procedure of an electrode lead into a cochlea of a recipient. This is because a surgeon may rely on evoked responses from the recipient to perform the insertion procedure effectively, and such evoked responses may only be properly detected and used when the cochlear implant system components are in alignment. Thus, during surgery, as well as in other circumstances, it may be desirable to achieve the highest degree of alignment possible to facilitate effective surgery and to promote reliable and power-efficient operation of the cochlear implant system.

To this end, disclosed systems and methods may be used to facilitate alignment of cochlear implant system components. For instance, an exemplary cochlear implant alignment system may include a cochlear implant system and a component alignment presentation system. The cochlear implant system may include a cochlear implant configured to be implanted under a skin flap of a recipient by way of an implantation procedure. The cochlear implant may be further configured to generate a wireless back telemetry signal during an insertion procedure that is performed subsequent to the implantation procedure. The cochlear implant system may further include an electrode lead permanently affixed to the cochlear implant. The electrode lead may be configured to be inserted into a cochlea of the recipient by way of the insertion procedure (i.e., to be inserted after the implantation procedure to implant the cochlear implant has been performed).

Additionally, the cochlear implant system may include a headpiece configured to operate external to the recipient (e.g., by residing at a position on the recipient's head). The headpiece may be configured to detect the wireless back telemetry signal generated by the cochlear implant. The detected back telemetry signal may have a signal strength indicative of a degree to which the headpiece is aligned with the cochlear implant, also referred to herein as a "degree of alignment" of the headpiece with the cochlear implant. For instance, if the back telemetry signal is transmitted at a known, fixed signal strength, then the signal strength that the back telemetry signal has when it is detected may indicate whether the receiver of the back telemetry signal included within the headpiece is well aligned with or poorly aligned with the transmitter of the back telemetry signal included within the cochlear implant. Specifically, if the signal strength is relatively strong, the headpiece may be determined to be relatively nearby the cochlear implant, which may indicate a good alignment. Conversely, if the signal strength is relatively weak, the headpiece may be determined to be further away from the cochlear implant, which may indicate a poorer alignment.

The cochlear implant system may further include a sound processor configured to generate a Received Signal Strength Indicator ("RSSI") signal based on the signal strength of the detected wireless back telemetry signal, as well as to provide the RSSI signal to the component alignment presentation system. The component alignment presentation system included within this exemplary cochlear implant alignment system may be communicatively coupled to, integrated with, built into, or otherwise associated with the cochlear implant system included within the cochlear implant alignment system and may include computer processing resources (e.g., at least one physical computing device). As such, the component alignment presentation system may be configured to receive the RSSI signal from the sound processor, and to present an indication of a degree of alignment of the headpiece with the cochlear implant based on the RSSI signal. For example, the component alignment presentation system may present the indication by way of a user interface (e.g., including graphics, sounds, haptic feedback, etc.) presented during the insertion procedure on a computer, on a mobile device, on the sound processor or the headpiece itself, or the like. Accordingly, and as will be made clear in the description below, the cochlear implant alignment system (and the user interface of the component alignment presentation system in particular) may assist a user associated with performing the insertion procedure (e.g., a surgeon or other member of the surgical team) in aligning the headpiece with the cochlear implant while the insertion procedure is underway.

Systems and methods for facilitating alignment of cochlear implant system components may provide various benefits. For example, disclosed methods and systems may assist users in aligning a headpiece of a cochlear implant system with a cochlear implant of the cochlear implant system without visibility of the recipient's head, without help from magnetic attraction forces pulling the components into place, or the like. Such assistance may be helpful and convenient in examples where visibility is poor, magnetic attraction forces are blunted or nonexistent, or in other such circumstances.

As one example, surgeons and others assisting the surgeon in implanting cochlear implant system components (e.g., performing lead insertion procedures to insert the electrode lead into the recipient's cochlea) may have various reasons to communicatively couple a headpiece with a cochlear implant during the surgery. For example, by communicatively coupling an external sound processor (e.g., by way of an external headpiece) with an internal cochlear implant, the sound processor may direct the cochlear implant to apply stimulation and/or detect voltages to indicate to the surgical team whether an electrode lead has been or is being inserted properly (e.g., based on detected impedances, evoked responses from the recipient, etc.). Unfortunately, operations in which data is obtained from a cochlear implant may use a relatively large amount of power, thereby requiring a relatively high degree of alignment between the headpiece and the cochlear implant to be performed successfully and reliably. Because various obstructions (e.g., surgical drapes, bandages, gauze, etc.) may limit visibility of and/or obstruct access to a location on the recipient's head where the cochlear implant is implanted, it has been inconvenient and frustrating for surgeons to try to achieve a reasonably high degree of alignment during surgery without significant tactile (e.g., magnetic) or visual feedback. Even if magnets are included on the headpiece and/or the cochlear implant to help facilitate the alignment, the magnetic attraction force may be blunted by the various layers of cloth, gauze, etc., between the headpiece and the cochlear implant. As such, systems and methods for facilitating alignment may be beneficial during surgery to make it easier to achieve the highest degree of alignment possible.

Outside of surgical applications, cochlear implant alignment systems may also be beneficial to recipients and their caregivers. For instance, certain cochlear implant systems may not provide significant magnetic alignment forces for a variety of reasons. For instance, magnets may be excluded from systems intended for recipients who find the attraction (e.g., the pinch) of a headpiece and a cochlear implant to be painful or uncomfortable, for recipients who have other medical devices which the magnets could interfere with, or for recipients who otherwise are unable or prefer not to use magnets. In other examples, magnets may lose their effectiveness over time such that the magnetic attraction force becomes too weak to hold the headpiece onto the head and/or to help guide the headpiece into place in alignment with the cochlear implant. Regardless of the reason, certain recipients may use means other than magnets to hold headpieces of their cochlear implant systems in place during normal, day-to-day operation. For example, a headpiece of a cochlear implant system may be held in place on the recipient's head with a hair clip, a headband, an adhesive, or the like. In these examples, users such as the recipient himself or herself and/or a caretaker assisting the recipient in positioning the headpiece may benefit from systems and methods described herein by receiving assistance in achieving and maintaining the highest degree of alignment possible to thereby ensure reliable, power-efficient operation of the cochlear implant system.

Systems and methods for facilitating alignment of cochlear implant system components may also be beneficial in that no additional circuitry may need to be added to cochlear implant systems in certain implementations for component alignment presentation systems to facilitate the alignment. Moreover, disclosed systems and methods may accomplish the ends described above without use of stronger magnets, without increasing transmission power levels, without increasing battery usage (i.e., to decrease battery time), and so forth.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary cochlear implant system 100. As shown, cochlear implant system 100 may include a microphone 102, a sound processor 104, a headpiece 106 having a coil disposed therein, a cochlear implant 108, and an electrode lead 110 having a plurality of electrodes 112. Additional or alternative components may be included within cochlear implant system 100 as may serve a particular implementation.

As shown, cochlear implant system 100 may include various components configured to be located external to a recipient including, but not limited to, microphone 102, sound processor 104, and headpiece 106. Cochlear implant system 100 may further include various components configured to be implanted within the recipient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a clinician's programming interface ("CPI") device, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") housing, an off the ear ("OTE") housing shared with headpiece 106, a body worn housing, etc.).

In some examples, sound processor 104 may wirelessly transmit stimulation parameters (e.g., in the form of data words included in a forward telemetry sequence) and/or power to cochlear implant 108 by way of a wireless communication link 114 between headpiece 106 and cochlear implant 108 (e.g., a wireless link between a coil disposed within headpiece 106 and a coil included within or coupled to cochlear implant 108). Wireless communication link 114 may be most reliable, effective, power efficient, and so forth, when headpiece 106 is aligned with cochlear implant 108 to the highest degree possible. In particular, wireless communication link 114 may be strongest when a communication component such as a coil disposed within headpiece 106 is aligned with and positioned as closely as possible to a communication component such as a coil disposed within cochlear implant 108 (e.g., positioned directly over the communication component of cochlear implant 108 on the other side of a skin flap of the recipient). It will be understood that communication link 114 may include a bi-directional communication link and/or one or more dedicated uni-directional communication links.

Headpiece 106 may be communicatively coupled to sound processor 104 and may include a communication component (e.g., an antenna coil and/or any other suitable wireless communication components) configured to facilitate selective wireless coupling of sound processor 104 to cochlear implant 108. Additionally or alternatively, headpiece 106 may be used to selectively and wirelessly couple external devices other than sound processor 104 (e.g., a battery charger, etc.) to cochlear implant 108. To this end, headpiece 106 may be configured to be affixed to the recipient's head and positioned or aligned such that a communication component housed within headpiece 106 is communicatively coupled to a corresponding implantable communication component included within or otherwise associated with cochlear implant 108. In this manner, stimulation parameters and/or power signals may be wirelessly transmitted between sound processor 104 and cochlear implant 108 via communication link 114.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the recipient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Electrode lead 110 may include the array of electrodes 112 disposed on a distal portion of electrode lead 110. Electrodes 112 may be configured to stimulate the cochlea after the distal portion of electrode lead 110 is inserted into the cochlea by way of an insertion procedure. It will be understood that one or more other electrodes (e.g., including a ground electrode, not explicitly shown) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea (i.e., after the distal portion of electrode lead 110 is inserted by way of the insertion procedure). As shown, electrode lead 110 may be pre-curved so as to properly fit within the spiral shape of the cochlea.

Along with receiving stimulation parameters and/or other instruction from sound processor 104 in a forward telemetry ("FTEL") signal, cochlear implant 108 may also transmit data back to sound processor 104 (e.g., by way of wireless communication link 114). For example, cochlear implant 108 may transmit a back telemetry ("BTEL") signal representative of measurements (e.g., impedance measurements, evoked response measurements, etc.) detected by cochlear implant 108 or representative of any other data that cochlear implant 108 may communicate with sound processor 104 in a particular implementation.

As shown, FIG. 1 illustrates that certain components of cochlear implant system 100 (i.e., microphone 102, sound processor 104, and headpiece 106) may be external components, while other components (i.e., cochlear implant 108, and lead 110 with electrodes 112) may be internal components. It will be understood, however, that in certain implementations of system 100, certain external components may be combined, omitted, and/or implanted within the recipient. For instance, in certain examples, sound processor 104 and headpiece 106 may be combined into a single unit embodied in a unified housing and that performs functions of both sound processor 104 and headpiece 106 as those functions have been described. Such a unit may be referred to as an OTE sound processor, an all-in-one sound processor, and active headpiece, or the like. As another example, sound processor 104 (e.g., including a rechargeable battery for powering sound processor 104) may be integrated within cochlear implant 108 as a fully-implantable cochlear implant system implanted within the recipient. In this example, a headpiece such as headpiece 106 may be used to provide power to the cochlear implant to charge a battery of the fully-implantable cochlear implant system.

Regardless of how cochlear implant system 100 is configured, however, systems and methods for facilitating alignment of cochlear implant system components may be equally applicable as long as there is some external component (referred to herein as the "headpiece") that is to be aligned with some internal component (referred to herein as the "cochlear implant").

Figure 2:
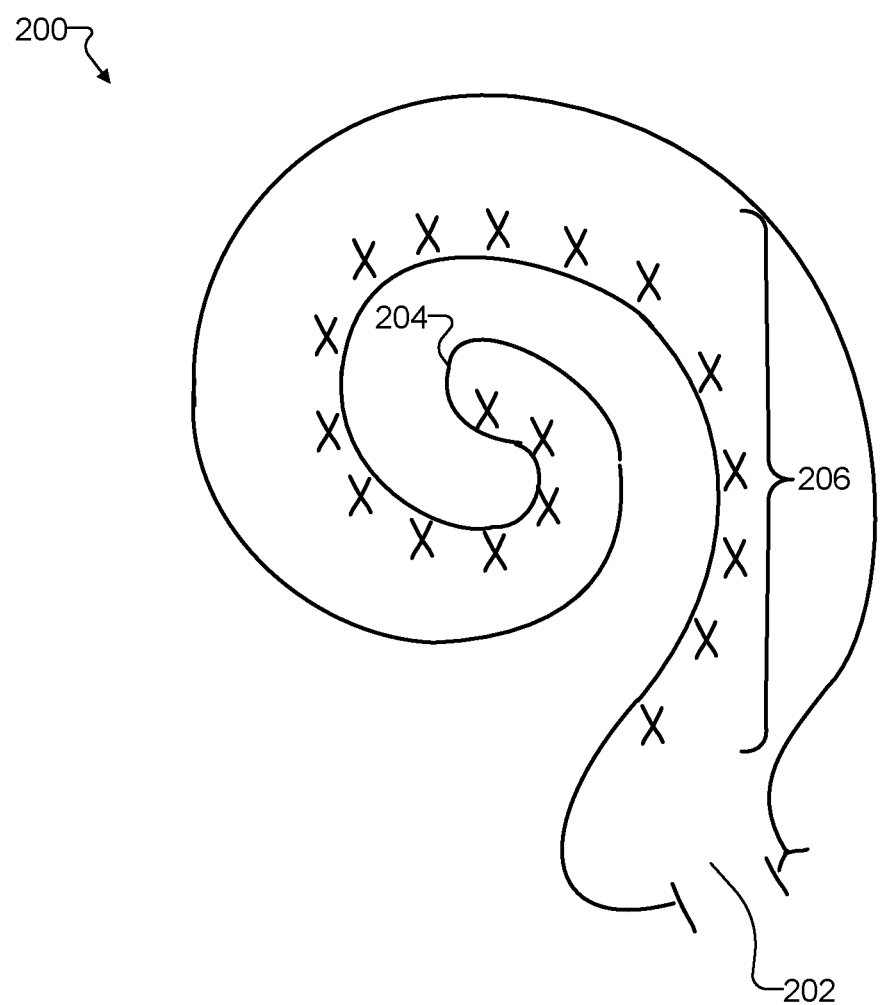
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the recipient perceiving relatively low frequencies and electrical stimulation applied by way of electrodes disposed within the basal region (i.e., "basal electrodes") may result in the recipient perceiving relatively high frequencies. The delineation between the apical and basal electrodes on a particular electrode lead may vary depending on the insertion depth of the electrode lead, the anatomy of the recipient's cochlea, and/or any other factor as may serve a particular implementation.

Figure 3:
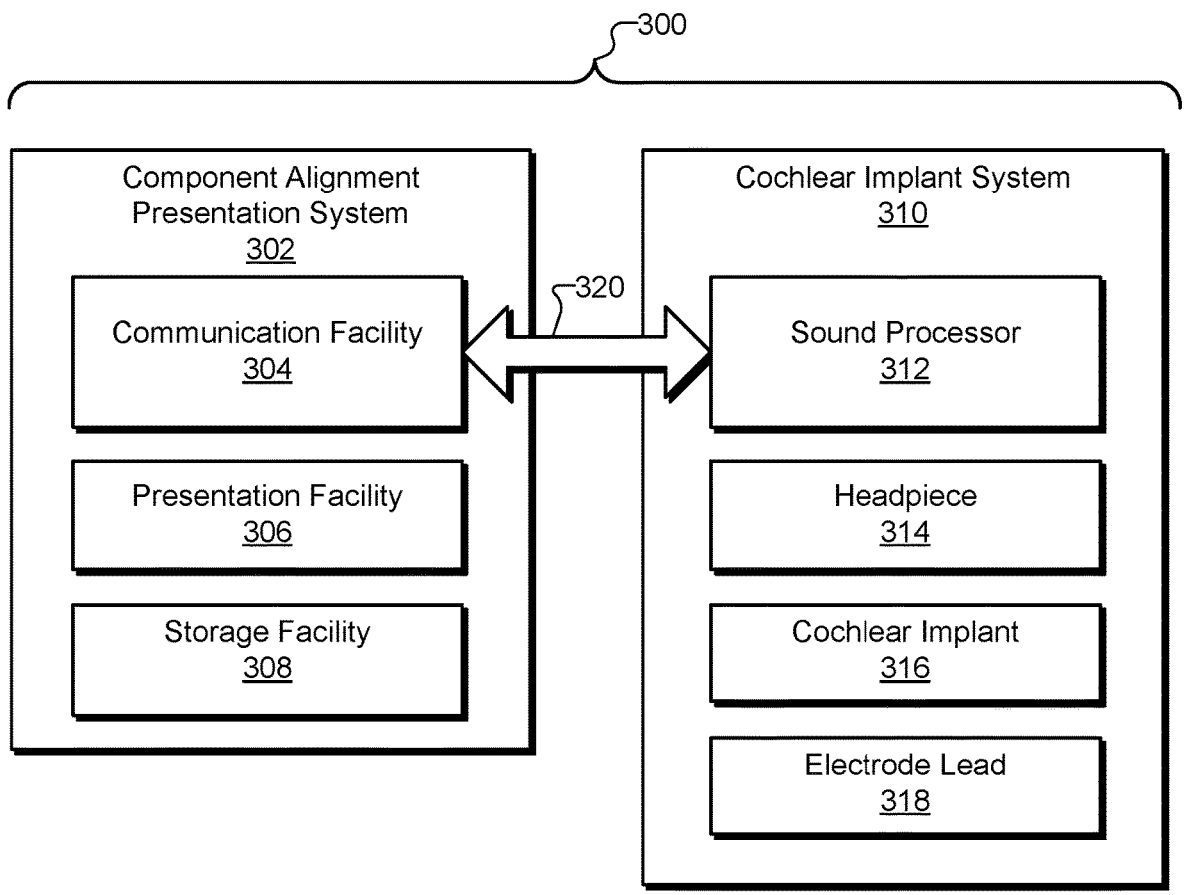
FIG. 3 illustrates a block diagram of an exemplary cochlear implant alignment system that includes a component alignment presentation system and a cochlear implant system and that is configured to facilitate alignment of components of the cochlear implant system according to principles described herein.

FIG. 3 illustrates a block diagram of an exemplary cochlear implant alignment system 300 ("system 300") that includes a component alignment presentation system and a cochlear implant system, and that is configured to facilitate alignment of components of the cochlear implant system. Specifically, as shown, a component alignment presentation system 302 within system 300 includes a communication facility 304, a presentation facility 306, and a storage facility 308. Component alignment presentation system 302 is communicatively coupled with a cochlear implant system 310 that includes a sound processor 312, a headpiece 314, a cochlear implant 316, and an electrode lead 318. Component alignment presentation system 302 and/or cochlear implant system 310 may interoperate with one another to perform any of the operations described herein for facilitating alignment of cochlear implant system components. To this end, as shown, communication facility 304, presentation facility 306, and storage facility 308 within system 300 may be selectively and communicatively coupled to one another, as may sound processor 312, headpiece 314, cochlear implant 316, and electrode lead 318 within cochlear implant system 310. Moreover, as illustrated by an arrow 320, certain components of component alignment presentation system 302 and cochlear implant system 310 (e.g., communication facility 304 and sound processor 312) may also be communicatively coupled with one another to implement intersystem communications as will be described below.

It will be recognized that although facilities 304 through 308 are shown to be separate facilities in FIG. 3, facilities 304 through 308 may be combined into fewer facilities, such as into a single facility, or divided into more facilities as may serve a particular implementation. Similarly, although components 312 through 318 are shown to be separate components in FIG. 3, components 312 through 316 may be combined into fewer components or divided into more components as may serve a particular implementation. Moreover, in certain examples, component alignment presentation system 302 and cochlear implant system 310 may be integrated together into a single system such that arrow 320, rather than representing a communicative coupling between separate systems, may represent the integration of a single system that performs all of the operations described below as being associated with both component alignment presentation system 302 and cochlear implant system 310. Each of facilities 304 through 308 and components 312 through 318 will now be described in more detail.

Communication facility 304 may include or be implemented by one or more physical computing devices (e.g., including hardware and/or software such as processors, memories, communication interfaces, instructions stored in memory for execution by the processors, etc.) that perform various operations associated with communicating with cochlear implant system 310 and/or components thereof. For example, communication facility 304 may receive an RSSI signal from cochlear implant system 310 that is based on a signal strength of a detected back telemetry signal, making the RSSI signal indicative of a degree of alignment of headpiece 314 with cochlear implant 316. Communication facility 304 may also transmit data to cochlear implant system 310 (e.g., data requesting or acknowledging the RSSI signal, etc.) and/or may perform any other operations to communicate with cochlear implant system 310 or other systems, or with a user of system 300, as may serve a particular implementation.

Presentation facility 306 may include or be implemented by one or more physical computing devices such as the same computing devices or similar (but separate) computing devices described above in relation to communication facility 304. Presentation facility 306 may generate and maintain a user interface by way of which a user of system 300 may provide input to or receive information from system 300. For example, based on the RSSI signal received by communication facility 304, presentation facility 306 may present to the user (e.g., by way of the user interface) an indication of a degree of alignment of headpiece 314 with cochlear implant 316 to assist the user in aligning headpiece 314 with cochlear implant 316. As will be described in more detail below, the user interface presented by presentation facility 306 may include graphics or text displayed on a screen, sounds presented by way of a loudspeaker, haptic or tactile feedback presented by way of an input/output device that the user may touch, and/or in any other suitable way.

Storage facility 308 may maintain any data received, generated, managed, maintained, used, and/or transmitted by facilities 304 and/or 306 in a particular implementation. For example, storage facility 308 may include data representative of RSSI signals received from cochlear implant system 310, data used to request such a signal, or the like. Additionally, storage facility 308 may include data representative of the user interface (e.g., including graphical data, sound data, etc.) that may be used to present the user interface and to thereby assist a user in aligning headpiece 314 with cochlear implant 316. Storage facility 308 may further include any other data as may serve a particular implementation of system 300 to facilitate performing one or more of the operations described herein.

Within cochlear implant system 310, sound processor 312 may be configured to perform basic signal processing such as to generate the RSSI signal based on a signal strength of a detected back telemetry signal, and may provide (i.e., communicate) the RSSI signal to communication facility 304 of system 300. Sound processor 312 may be implemented by sound processor 104, described above, or a similar component. In some examples, sound processor 312 may receive the detected back telemetry signal having the signal strength indicative of the degree of alignment of headpiece 314 with cochlear implant 316, amplify the back telemetry signal, filter and/or otherwise process the back telemetry signal, and then convert the back telemetry signal from an analog signal to a digital RSSI signal that represents the signal strength of the detected back telemetry signal. Sound processor 312 may also perform various other operations such as those described above in relation to sound processor 104.

Headpiece 314 may be configured to operate external to the recipient and may be aligned with cochlear implant 316 in order to facilitate communication with cochlear implant 316. Headpiece 314 may be implemented by headpiece 106, described above, or a similar component. Headpiece 314 may be configured to detect the back telemetry signal generated by cochlear implant 316 and to provide the back telemetry signal (e.g., or at least a signal representative of the detected signal strength of the detected back telemetry signal) to sound processor 312. As such, headpiece 314 may include a wireless communication component such as an antenna coil and may be communicatively coupled (e.g., by way of a cable) to sound processor 312. Headpiece 314 may also perform various other operations such as those described herein in relation to headpiece 106.

Cochlear implant 316 may be configured to be implanted within the recipient (e.g., under a skin flap of the recipient) and to communicate with (e.g., receive forward telemetry signals from and/or send back telemetry signals to) headpiece 314 when headpiece 314 and cochlear implant 316 are suitably aligned. For example, cochlear implant 316 may be configured to generate a wireless back telemetry signal subsequent to being implanted in the recipient by way of an implantation procedure. Cochlear implant 316 may be implemented by cochlear implant 108, described above, or a similar component. As described above, wireless transcutaneous communication may be most effective when the alignment of headpiece 314 and cochlear implant 316 is optimized (i.e., by bringing the components as close together as possible). Thus, cochlear implant 316 may generate and transmit a back telemetry signal with a known, fixed signal strength such that, when the back telemetry signal is detected by headpiece 314, the detected signal strength will be indicative of a degree of alignment of headpiece 314 with cochlear implant 316. Cochlear implant 316 may also perform various other operations such as those described herein in relation to cochlear implant 108.

Electrode lead 318 may be permanently affixed to cochlear implant 316 and may be configured to be inserted into a cochlea of the recipient by way of an insertion procedure. The insertion procedure by way of which electrode lead 318 is inserted into the cochlea may be performed subsequent to the implantation procedure by way of which cochlear implant 316 is implanted. As such, when the insertion procedure is underway, cochlear implant 316 may be already implanted and operational to generate and provide the wireless back telemetry signal that will ultimately allow component alignment presentation system 302 to present the indication of the degree of alignment of headpiece 314 aligned with cochlear implant 316. This may be beneficial for users associated with performing the insertion procedure (e.g., a surgeon or others on a surgical team) because feedback provided by electrode lead 318 may be instrumental in helping the users perform an effective and successful insertion procedure, but such feedback is only properly received when the users are able to align headpiece 314 to cochlear implant 316.

Feedback provided by electrode lead 318 to help enable a surgeon or surgical team to effectively insert electrode lead 318 into the cochlea of the recipient may take various forms and may facilitate the surgery in various ways. Electrodes included on electrode lead 318 may facilitate detecting, for example, an evoked response, an impedance, or the like that may be used to provide real-time feedback to the surgical team to facilitate effective performance of the insertion procedure. In one particular example, for instance, system 300 may further include a loudspeaker (e.g., included within component alignment presentation system 302 or cochlear implant system 310) that may be configured to apply acoustic stimulation (e.g., one or more acoustic pulses, etc.) to the recipient during the insertion procedure. In this example, sound processor 312 may be further configured, when headpiece 314 is aligned with cochlear implant 316, to detect an evoked response of the recipient that occurs in response to the acoustic stimulation applied to the recipient, and to provide the detected evoked response to an insertion procedure assistance system associated with the cochlear implant system and configured to assist the user in performing the insertion procedure.

In this example, the acoustic stimulation may cause an evoked response to occur (e.g., to be involuntarily generated by the recipient) that may be detected by electrodes included on electrode lead 318 as electrode lead 318 is being inserted into the cochlea. The evoked response may be any type of evoked response as may serve a particular implementation. For example, as used herein, an "evoked response" may refer to an electrocochleographic ("ECoG") potential, an auditory nerve response, a brainstem response, a compound action potential, and/or any other type of neural or physiological response that may occur within a patient in response to application of acoustic stimulation to the patient. In some examples, evoked responses may originate from neural tissues, hair cell to neural synapses, inner or outer hair cells, or other sources.

Accordingly, as used herein, an "insertion procedure assistance system" may refer to any system that may be configured to access or receive data representative of an evoked response, and to employ this data to assist the surgical team in performing the insertion procedure in any way. Such systems are described, for example, in co-pending PCT Application No. PCT/US16/15203, filed Jan. 27, 2016, and entitled SYSTEMS AND METHODS FOR INTRA-SURGICAL MONITORING OF COCHLEAR TRAUMA DURING AN ELECTRODE LEAD INSERTION PROCEDURE, where insertion procedure assistance systems (e.g., sometimes referred to as monitoring systems) use evoked responses to monitor cochlear trauma during insertion procedures. Other exemplary insertion procedure assistance systems (e.g., sometimes referred to as scalar translocation detection systems) are described in co-pending PCT Application No. PCT/US17/48973, filed Aug. 28, 2017, and entitled SYSTEMS AND METHODS FOR DETECTING A SCALAR TRANSLOCATION OF AN ELECTRODE LEAD WITHIN A COCHLEA OF A COCHLEAR IMPLANT PATIENT. In this case, the disclosed systems are configured to perform real-time detection of scalar translocation, which is a particular type of cochlear trauma suffered by certain cochlear implant recipients (patients) during insertion procedures.

Moreover, just as evoked responses detectable using electrode lead 318 are used to facilitate insertion procedures when headpiece 314 and cochlear implant 316 are properly aligned, measurements of tissue impedances and/or other measurements performed using electrode lead 318 may also facilitate insertion procedures when headpiece 314 and cochlear implant 316 are properly aligned. For example, insertion procedure assistance systems (e.g., sometimes referred to as electrode locating systems) are described in co-pending PCT Application No. PCT/US17/49792, filed Aug. 31, 2017, and entitled ELECTRODE LOCATING SYSTEMS AND METHODS FOR USE WITHIN A COCHLEAR IMPLANT PATIENT. These insertion procedure assistance systems direct electrodes to generate electrical pulses such that excitation spread measurements may be performed to determine where the electrodes are located within the cochlea during insertion procedures. As another example, insertion procedure assistance systems (e.g., sometimes referred to as proximity detection systems) are described in co-pending PCT Application No. PCT/US18/38345, filed Jun. 19, 2018, and entitled SYSTEMS AND METHODS FOR DETECTING ELECTRODE LEAD PROXIMITY TO COCHLEAR TISSUE. These insertion procedure assistance systems direct electrodes to apply pulses during insertion procedures to thereby form dipoles that generate fields detectable by other electrodes to thereby determine the proximity of electrode leads to cochlear tissue.

A relatively high degree of alignment between headpiece 314 and cochlear implant 316 may allow each of these and other suitable insertion procedure assistance systems to use electrode lead 318 to perform their respective roles in facilitating insertion procedures. As such, the contents of all of the co-pending PCT Applications mentioned above are hereby incorporated by reference in their entirety.

Figure 4:
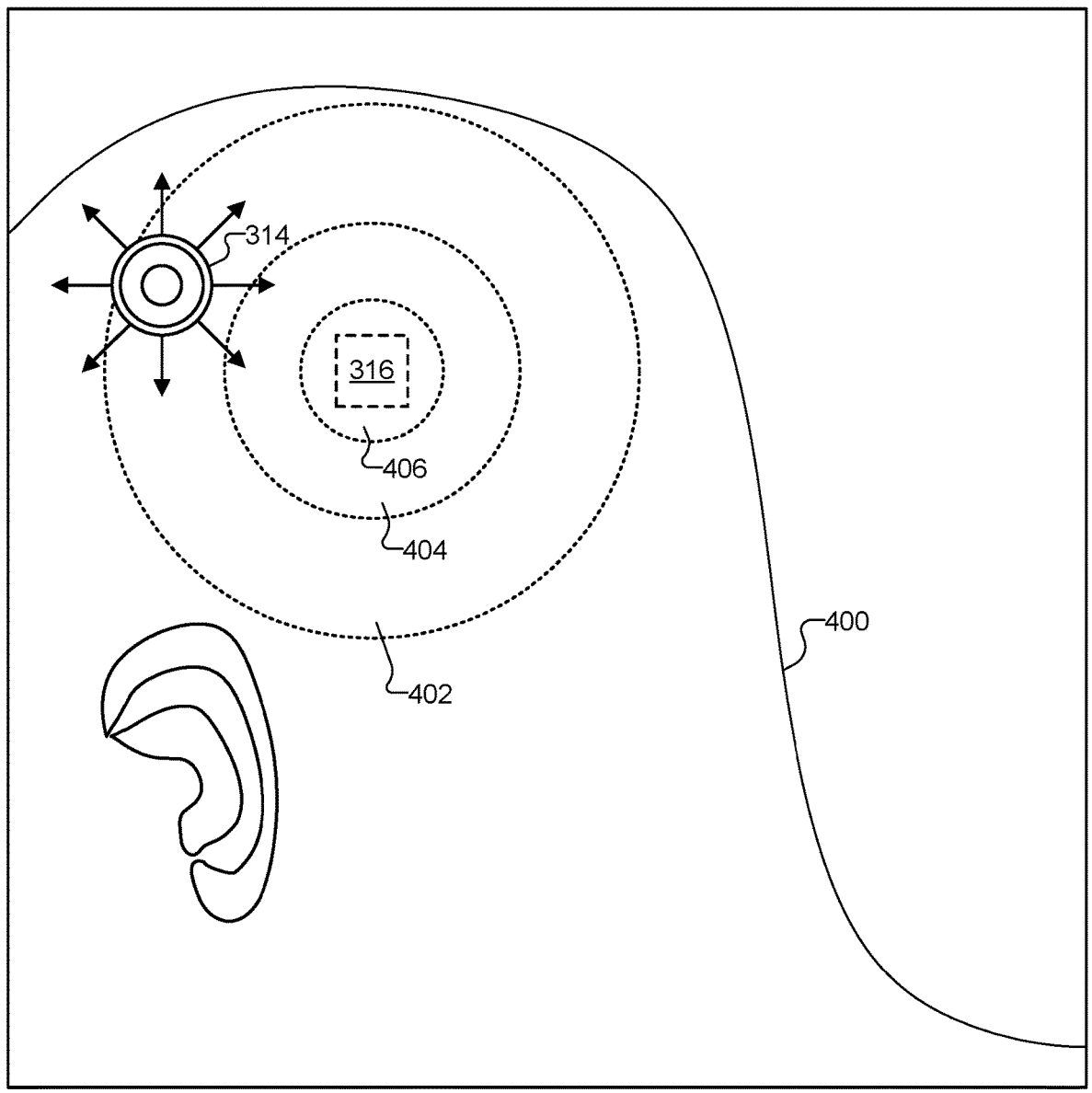
FIG. 4 illustrates exemplary aspects of how the component alignment presentation system of FIG. 3 may facilitate alignment of a headpiece of the cochlear implant system of FIG. 3 with a cochlear implant of the cochlear implant system according to principles described herein.

FIG. 4 illustrates exemplary aspects of how component alignment presentation system 302 may facilitate alignment of headpiece 314 with cochlear implant 316 of cochlear implant system 310. Cochlear implant 316 may be implanted beneath a skin flap on a particular part of a head of a recipient 400. To illustrate, cochlear implant 316 is depicted in FIG. 4 using dashed lines to indicate that cochlear implant 316 is beneath the skin and may not actually be visible from the external perspective shown in FIG. 4. A user of system 300 (e.g., a surgeon or the like) may wish to determine where cochlear implant 316 is located so as to align headpiece 314 with cochlear implant 316 to the highest degree possible (e.g., while an insertion procedure is underway). While headpiece 314 is shown to be "floating" on the surface of the head of recipient 400 (i.e., so as to have complete freedom of movement in any direction), it will be understood that headpiece 314 may actually be somewhat limited in its movement as a result of being tethered (e.g., by a communication cable) to other components of cochlear implant system 310 such as sound processor 312 (e.g., a sound processor or the like), which is not explicitly shown in FIG. 4 but which may be disposed, for example, behind the ear of recipient 400.

In order to achieve an alignment, the user may manually attempt to move headpiece 314 into alignment with cochlear implant 316. As such, the user may bring headpiece 314 into the general vicinity of cochlear implant 316. For example, as shown, the user may bring headpiece 314 into a region 402 which may cover a relatively large portion of the head of recipient 400 (i.e., making the region easy to locate), but which may encompass areas that are not particularly well-aligned with cochlear implant 316. Region 402 may represent a region in which cochlear implant 316 is capable of receiving, to a least a certain degree, a forward telemetry signal generated by headpiece 314. For example, when cochlear implant system 310 is being initiated and headpiece 314 has not yet made a strong connection with cochlear implant 316, cochlear implant system 310 may cause a relatively large amount of power to be emitted from headpiece 314 to allow cochlear implant 316 to receive power and begin powering up and transmitting a back telemetry signal.

As such, when headpiece 314 is located within an outer portion of region 402, headpiece 314 may not be aligned with cochlear implant 316 to a particularly large degree, but may be aligned well enough to receive power from the forward telemetry signal and begin operating to generate and transmit the back telemetry signal. However, while headpiece 314 remains along the outer portion of region 402, the detected signal strength that headpiece 314 detects for the back telemetry signal may indicate that there is still a relatively low degree of alignment. As a result, as will be described in more detail below, a sound processor communicatively coupled with headpiece 314 (e.g., sound processor 312) may generate and provide an RSSI signal indicating that there is still a relatively low degree of alignment, which may be presented to the user in any of a variety of ways described herein. Based on the presentation of the indication that there is a relatively low degree of alignment, the user may continue moving headpiece 314 around on the head of recipient 400 and monitoring the user interface to determine if the degree of alignment of headpiece 314 with cochlear implant 316 is increasing or decreasing.

For example, if the user moves headpiece 314 into a region 404 that has a higher degree of alignment than the outer portion of region 402, the back telemetry signal detected by headpiece 314 may have a stronger signal strength, indicating that the degree of alignment is increasing. This improvement in the alignment may be communicated to the user by a similar chain of operations as described above (e.g., by way of the RSSI signal, the user interface, etc.) so that the user knows that the degree of alignment of headpiece 314 is increasing. It will be understood that, while discrete regions 402 and 406 are shown in FIG. 4, that the proximity of headpiece 314 to cochlear implant 316 may, in some examples, be represented by a different (e.g., larger) number of discrete regions, or by a continuum. By presenting feedback with a finer resolution in this way, the user may more quickly and easily determine how to move headpiece 314 to achieve the highest degree of alignment possible.

Based on feedback presented by component alignment presentation system 302 as described above, the user may eventually move headpiece 314 directly over cochlear implant 316 within a region 406. Within region 406, the degree of alignment between headpiece 314 and cochlear implant 316 may be sufficient for cochlear implant system 310 to perform operations to finalize an initialization process and to lock the communication between the components, as will be described below. Additionally, component alignment presentation system 302 may indicate to the user that the sufficient degree of alignment has been achieved so that the user may cease moving headpiece 314 around and may fix headpiece 314 at the aligned location over cochlear implant 316 (e.g., by holding headpiece 314 in place, fixing it using mechanical or adhesive means, or the like). In some examples, when headpiece 314 is moved into place within region 406, a magnetic attraction force between components 314 and 316 may be strong enough to pull the components together and hold headpiece 314 in place.

Component alignment presentation system 302 may be used in conjunction with cochlear implant system 310 to facilitate alignment of cochlear implant system components in various situations and circumstances. For instance, in one example as mentioned above, the user aligning headpiece 314 with cochlear implant 316 by assistance of component alignment presentation system 302 may be associated with performing a surgical insertion procedure whereby electrode lead 318 is inserted into a cochlea of recipient 400. The insertion procedure may take place subsequent to a surgical implantation procedure by way of which cochlear implant 316 is implanted within recipient 400. In this way, cochlear implant 316 may already be in place during the insertion procedure so as to provide the wireless back telemetry signal for headpiece 314 to detect as described herein. In some examples, a surgeon (or another surgical team member) may have poor visibility and/or access to the area of the head where cochlear implant 316 is implanted due to various obstructions (e.g., bandages, drapes, etc.) that are located around that area. Thus, as the surgeon moves headpiece 314 around to attempt to achieve alignment with cochlear implant 316, component alignment presentation system 302 may receive the RSSI signal from cochlear implant system 310 and may present live, real-time, updated information to the surgeon to indicate a degree of alignment of headpiece 314 with cochlear implant 316 while the insertion procedure is underway.

As another example, also mentioned above, a user aligning headpiece 314 with cochlear implant 316 by assistance of component alignment presentation system 302 may be recipient 400, or a caregiver assisting recipient 400, at a time subsequent to the insertion procedure (e.g., after cochlear implant system 310 has been successfully installed and recipient is using cochlear implant system 310 for daily normal operation). For example, if cochlear implant system 310 is not implemented with magnets in components 314 and/or 316 due to a sensitivity of recipient 400 or the like, or if magnets are (or have become) too weak to be particularly helpful to recipient 400 in achieving a reasonable degree of alignment of components 314 and 316, component alignment presentation system 302 may assist recipient 400 in aligning headpiece 314 with cochlear implant 316 in any of the ways described above. Specifically, component alignment presentation system 302 may receive the RSSI signal from cochlear implant system 310 and may present the indication of the degree of alignment of headpiece 314 with cochlear implant 316 to recipient 400 when cochlear implant system 310 is under control of recipient 400 subsequent to the insertion procedure whereby electrode lead 318 is inserted into the cochlea of recipient 400.

Figure 5:
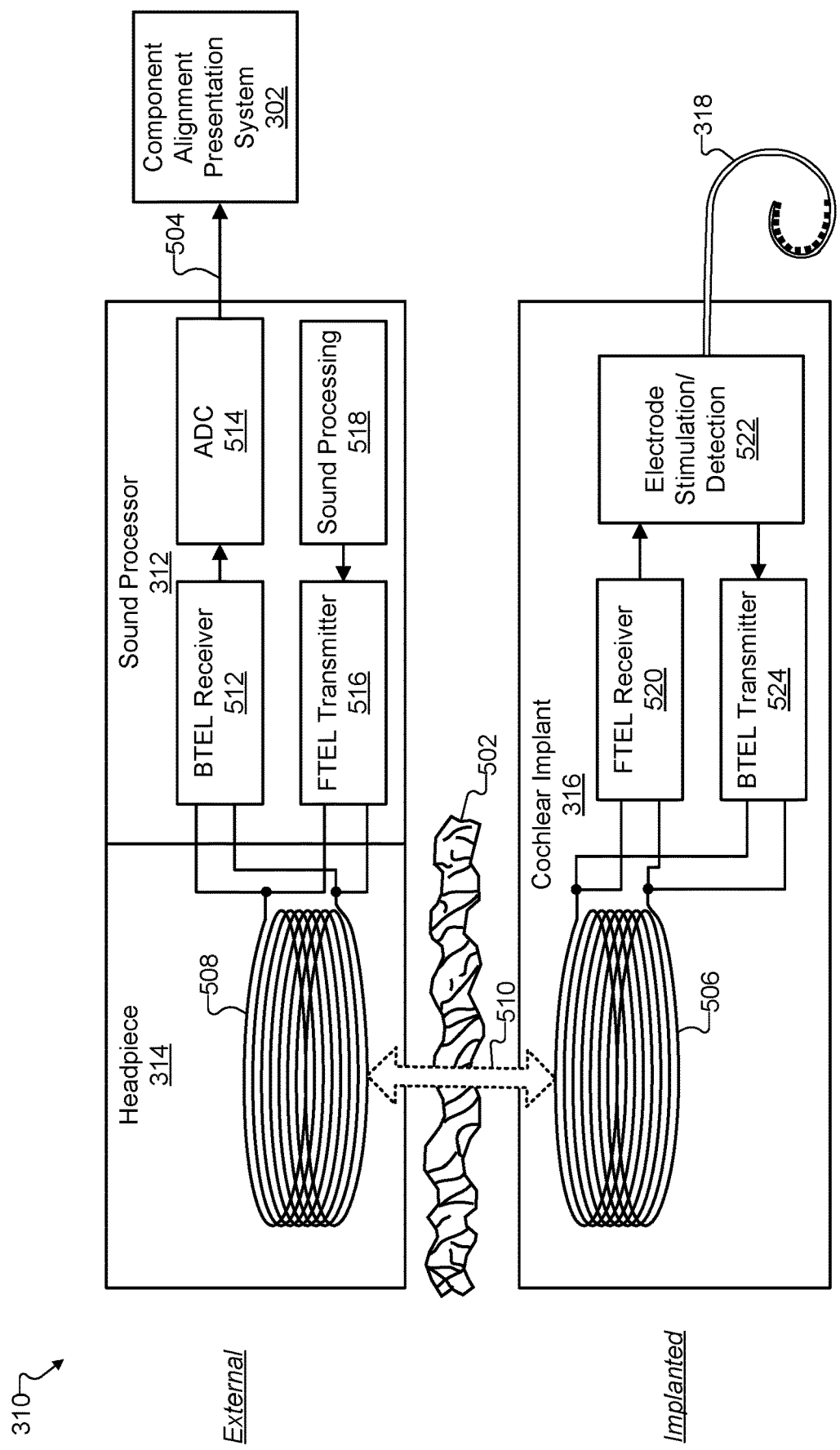
FIG. 5 illustrates exemplary aspects of the cochlear implant system of FIG. 3 during operation with the component alignment presentation system of FIG. 3 according to principles described herein.

FIG. 5 illustrates exemplary aspects of cochlear implant system 310 during operation with component alignment presentation system 302 within system 300. Specifically, as shown, headpiece 314 is located external to a recipient on the other side of a skin flap 502 from cochlear implant 316, which is implanted within the recipient. Headpiece 314 is communicatively coupled with sound processor 312, which is also external to the recipient in this configuration, and which generates an RSSI signal 504 and provides RSSI signal 504 to component alignment presentation system 302. The providing of RSSI signal 504 may allow component alignment presentation system 302 to present an indication, based on RSSI signal 504, of a degree of alignment of headpiece 314 with cochlear implant 316 to assist a user in aligning components 314 and 316.

As shown, cochlear implant 316 may be configured to be implanted within the recipient's head under skin flap 502 and to communicate with headpiece 314 by way of a first communication component 506 (e.g., an antenna coil or the like) included within cochlear implant 316 when headpiece 314 is aligned with cochlear implant 316. Headpiece 314 may be configured to be disposed on the recipient's head on an opposite side of skin flap 502 from the cochlear implant and to communicate with the cochlear implant by way of a second communication component 508 (e.g., another antenna coil or the like) included within headpiece 314 when headpiece 314 is aligned with cochlear implant 316. Sound processor 312 may be communicatively coupled with headpiece 314 (e.g., by way of a cable or the like) and with component alignment presentation system 302. Sound processor 312 may be configured to communicate with cochlear implant 316 by way of the headpiece.

While an internal cochlear implant and an separated external headpiece and sound processor are depicted FIG. 5 as one exemplary embodiment of cochlear implant system 310, it will be understood that, in other examples, cochlear implant system components 312 through 316 may be implemented by other components and/or in other ways. For instance, as mentioned above, in certain examples, sound processor 312 and headpiece 314 may be integrated together into an integrated or off-the-ear sound processor (or active headpiece) in a cochlear implant system that does not employ a separate headpiece. In other words, the integrated sound processor may include communication component 508 as well as the circuitry and functionality of sound processor 312 such that no separate headpiece is required. In still other examples, cochlear implant 316 may incorporate all the functionality of both cochlear implant 108 and sound processor 104, which may all be implanted within the recipient. Such a system may be referred to as a fully implantable cochlear implant system. The internal sound processor/cochlear implant combination of such a fully implantable cochlear implant system may be recharged by a battery charger or the like, which may implement (e.g., in separate components or as one integrated component) headpiece 314, sound processor 312, and any or all of the circuitry and functionality described to be included therein.

Regardless of how components 312 through 316 are implemented and/or what roles these components take in a particular implementation of cochlear implant system 310, certain circuitry and/or functionality may be included within each of the components to allow the components to facilitate alignment along with component alignment presentation system 302. For example, as shown, communication component 506 may be included within cochlear implant 316 and communication component 508 may be included within headpiece 314. By way of these communication components, headpiece 314 and cochlear implant 316 may transmit and receive both forward telemetry signals and back telemetry signals over a wireless communication link 510 (e.g., similar to wireless communication link 114). Moreover, as shown, sound processor 312 may include a back telemetry receiver 512 ("BTEL receiver 512"), an analog-to-digital conversion facility 514 ("ADC 514"), a forward telemetry transmitter 516 ("FTEL transmitter 516"), and a sound processing facility 518 ("sound processing 518"). Cochlear implant 316 may include a forward telemetry receiver 520 ("FTEL receiver 520"), electrode stimulation and detection circuitry 522 ("electrode circuitry 522"), and a back telemetry transmitter 524 ("BTEL transmitter 524").

In operation, once headpiece 314 and cochlear implant 316 are closely enough aligned that cochlear implant 316 receives operating power from headpiece 314 (e.g., once headpiece 314 is approximately located within region 402) BTEL transmitter 524 may generate and transmit a back telemetry signal over wireless communication link 510 (e.g., by way of communication component 506). The back telemetry signal, as generated by BTEL transmitter 524, may be transmitted at a signal strength that is fixed (i.e., at a constant, known, and/or expected magnitude). BTEL receiver 512 may receive the back telemetry signal and perform amplification operations, filtering operations, and/or other suitable signal processing on the back telemetry signal. As detected by BTEL receiver 512, the signal strength of the detected back telemetry signal may be indicative of a degree of alignment of headpiece 314 is aligned with cochlear implant 316 as a result of the back telemetry signal being generated (e.g., by BTEL transmitter 524) at the fixed transmitted signal strength.

Once the back telemetry signal has been suitably processed by BTEL receiver 512, ADC 514 may generate RSSI signal 504 as a digital signal by performing an analog-to-digital conversion of an analog signal representative of the signal strength of the detected back telemetry signal. As shown, ADC 514 (e.g., or a communication facility included within cochlear implant system 310, not explicitly shown) may then provide RSSI signal 504 to component alignment presentation system 302 so that the alignment indication may be presented, by component alignment presentation system 302, to a user attempting to optimize the alignment between headpiece 314 and cochlear implant 316.

Along with the back telemetry communication specifically employed to facilitate the alignment of cochlear implant system components described above, it will be understood that forward telemetry communication may also take place in order for cochlear implant system 310 to properly function as a cochlear implant system (e.g., similar to cochlear implant system 100 described above). For example, along with receiving the back telemetry signal from cochlear implant 316, headpiece 314 may be further configured to transmit a wireless forward telemetry signal to cochlear implant 316 concurrently with the detection of the back telemetry signal generated by cochlear implant 316. Specifically, sound processing 518 may represent various operations performed by a sound processor such as sound processor 108, described above. Based on instruction from sound processing 518, FTEL transmitter 516 may transmit power (e.g., operating power) and/or data (e.g., stimulation parameters and instructions) over wireless communication link 510 for use by cochlear implant 316. The forward telemetry signal transmitted by FTEL transmitter 516 may be received within cochlear implant 316 by FTEL receiver 520. The power received may be used as operating power for cochlear implant 316 (e.g., which may not have a battery or other power supply and may rely on power within the forward telemetry signal as its only source of power). The data received within the forward telemetry signal may be used by electrode circuitry 522 to apply stimulation to the recipient by way of electrode lead 318. Electrode circuitry 522 may also use electrode lead 318 to detect data (e.g., evoked responses, impedances, etc.) in any of the ways described herein. For instance, such data may be included within the back telemetry signal transmitted back to sound processor 312 by way of cochlear implant 316 and headpiece 314.

In order for the forward telemetry signal and the back telemetry signal to be transmitted concurrently (e.g., simultaneously using full-duplex communication) by way of communication components 506 and 508, the forward telemetry signal may be transmitted at a different frequency than the back telemetry signal. For example, the forward telemetry signal may be transmitted at a frequency such as 49 MHz, while the back telemetry signal may be transmitted at a different frequency such as 10.7 MHz in one particular example.

As described above, the degree of alignment of components 314 and 316 may be determined based on a detected signal strength of a back telemetry signal transmitted by cochlear implant 316. However, in certain examples, it may be possible to determine the degree of alignment of the components in a similar way using a detected signal strength of the forward telemetry signal. For example, cochlear implant 316 could detect the signal strength of a forward telemetry signal sent by headpiece 314, process and convert the detected signal strength to a digital RSSI signal in a similar way as described above for sound processor 312, and transmit the RSSI signal to headpiece 314. It will be understood that, while this exemplary implementation or one similar to it may be possible, it may be preferable in certain examples to detect the signal strength of a back telemetry signal rather than a forward telemetry signal because, as described above, the forward telemetry signal may have a variable signal strength (e.g., to transmit more power before a high degree of alignment has been achieved than after), while the back telemetry signal may be transmitted with a fixed signal strength that is more directly correlated with the degree of alignment.

One reason that the signal strength of the forward telemetry signal may be variable, rather than fixed (as may be the case with the back telemetry signal), is that more transmission power may be called for while headpiece 314 is still being moved around in search of a high degree of alignment than when the high degree of alignment has been achieved. For example, while the high degree of alignment is being pursued (e.g., while headpiece 314 is being moved around within region 402 to try to find region 406 in the center), sound processor 312 may be configured to perform an initial system communication characterization. Specifically, the communication characterization may be performed when sound processor 312 determines that a particular degree of alignment has been reached by, for instance, detecting that a signal strength of the back telemetry signal is at a particular level, detecting that a user has manually indicated (e.g., by a button press or the like) that the components cannot be aligned any better, or the like. Once sound processor 312 determines that the particular degree of alignment is reached, sound processor 312 may characterize the forward telemetry signal levels being transmitted to determine power levels at which intersystem communications (e.g., over wireless communication link 510) will be made during operation of cochlear implant system 310.

In conventional systems, this system communication characterization may only be performed once at the initialization (e.g., power on, link startup, etc.) of the sound processor. For configurations in which magnetic forces automatically maintain the alignment between components 314 and 316, such a one-time characterization may be appropriate. However, in configurations in which magnetic forces are absent or less capable of maintaining the initial alignment (e.g., configurations of magnet-less systems, surgical configurations where obstructions blunt the magnetic forces, etc.), it may be desirable to track whether the initial system communication characterization remains accurate (e.g., whether the alignment drifts or the like) and to recharacterize the system at a time other than during the initialization if it is detected that the initial system characterization is no longer accurate. To this end, sound processor 312 may determine (e.g., during the operation of cochlear implant system 310) that the determined power levels are non-optimal based on RSSI signal 504. Sound processor 312 may then perform a system communication recharacterization to determine optimal power levels at which intersystem communications will be made during subsequent operation of cochlear implant system 310.

Just as RSSI signal 504 may be used to help optimize power usage by facilitating system recharacterization when needed, as described above, various examples may further use RSSI signal 504 for other purposes besides assisting users in aligning headpiece 314 with cochlear implant 316. For example, in certain implementations, RSSI signal 504 may be used to monitor and track the thickness of skin flap 502 over time. For example, by periodically logging a value of RSSI signal 504 (e.g., even in a standard system in which headpiece 314 is aligned and held in place using magnetic forces), the relative thickness of skin flap 502 may be tracked. For example, if it is determined that RSSI signal 504 has gradually indicated a lower degree of alignment in a system where magnets have held headpiece 314 in place, this may indicate that scar tissue or the like has caused skin flap 502 to thicken such that headpiece 314 no longer has as strong of a connection with cochlear implant 316. Similarly, the gradual decrease of RSSI signal 504 may indicate that a cable between sound processor 312 and headpiece 314 has degraded or been damaged such that some of the power generated by FTEL transmitter 516 is being lost in the cable rather than being transmitted to cochlear implant 316 by way of headpiece 314. In these and other suitable applications of RSSI signal 504, the information determined by tracking signal 504 may be useful for recipients and/or their caregivers and physicians to diagnose problems with cochlear implant system 310 that may be remedied to improve the functionality of cochlear implant system 310.

As mentioned above, system 300 may be implemented in a variety of different ways. For example, component alignment presentation system 302 may be entirely integrated within cochlear implant system 310, may be an entirely separate and distinct system from cochlear implant system 310, or a hybrid approach may be employed in which certain functionality of component alignment presentation system 302 is integrated with cochlear implant system 310 and other functionality is performed separately. Accordingly, to illustrate a few specific ways that system 300 may be implemented, FIGS. 6A through 6C show exemplary implementations and configurations of system 300 (not explicitly labeled) and, specifically, how component alignment presentation system 302 may integrate and/or interact with cochlear implant system 310.

Figure 6A:
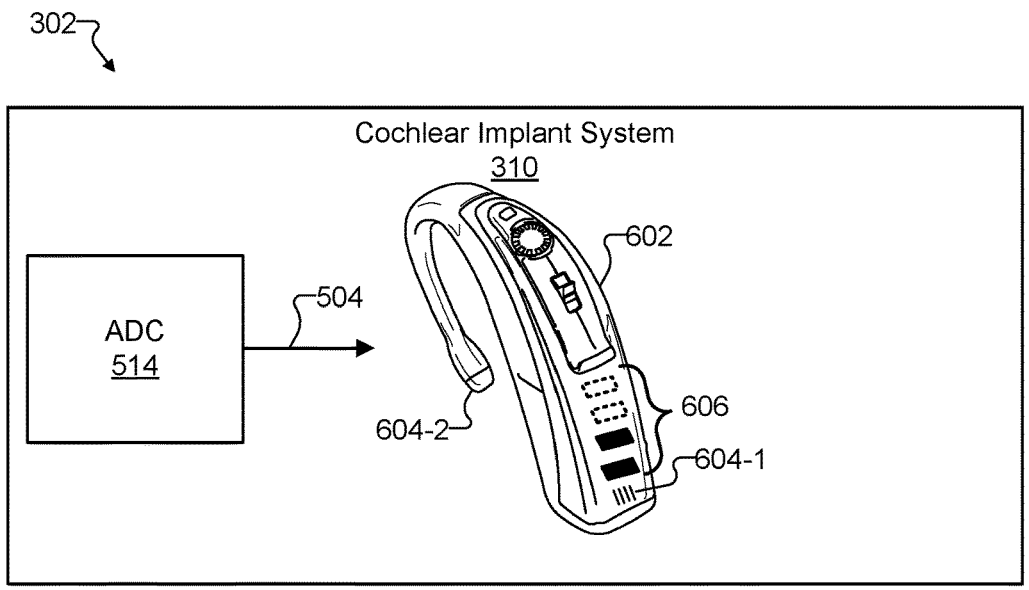
FIGS. 6A through 6C illustrate exemplary implementations and configurations of the cochlear implant system and the component alignment presentation system of FIG. 3 according to principles described herein.

As shown in FIG. 6A, component alignment presentation system 302 may be completely integrated with (e.g., implemented within) cochlear implant system 310. For example, component alignment presentation system 302 may be implemented within a sound processor of cochlear implant system 310 such as a BTE sound processor 602. As such, component alignment presentation system 302 may use components of cochlear implant system 310 itself to indicate to the user the degree of alignment of headpiece 314 with cochlear implant 316. Such cochlear implant system components could include, for example, components of sound processor 602, such as a loudspeaker 604 (e.g., a loudspeaker 604-1 that emits sounds to be heard not only by the recipient but also, for example, by a caretaker associated with the recipient; a loudspeaker 604-2 that emits sounds directly to the recipient to be heard by the recipient using residual hearing that the recipient retains; etc.) and/or one or more visual indicators 606 (e.g., implemented by light-emitting diodes (LEDs) or the like). As shown in FIG. 6A, component alignment presentation system 302 may receive RSSI signal 504 from ADC 514 as described above, and may use one or both of loudspeakers 604 and/or visual indicators 606 to indicate the degree of alignment based on RSSI signal 504. It will be understood that, while ADC 514 is shown as being included within cochlear implant system 310 along with sound processor 602 in FIG. 6A, ADC 514 may actually be integrated into sound processor 602 and may provide RSSI signal 504 to system 300 by providing the signal to other components included within sound processor 602 (e.g., a microprocessor or the like).

Figure 6B:
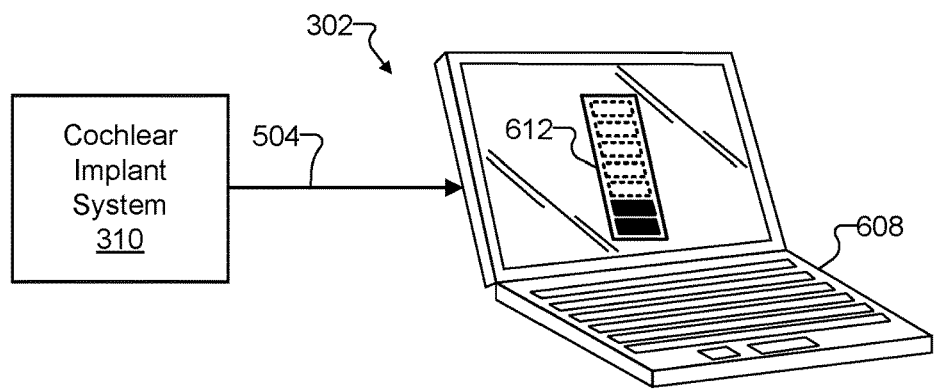
Figure 6C:
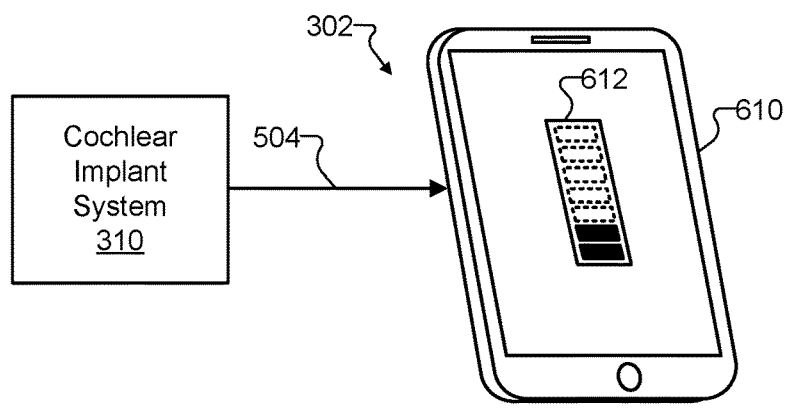

As additional examples, FIGS. 6B and 6C show implementations of system 300 where the user interface by way of which component alignment presentation system 302 presents the indication of the degree of alignment of headpiece 314 with cochlear implant 316 is implemented, respectively, by communication devices 608 and 610, which are each separate from and communicatively coupled with cochlear implant system 310. Communication devices 608 and 610 may be any suitable devices capable of communicating with cochlear implant system 310 (e.g., by way of a cable or wireless means, directly or by way of another intermediary device, etc.) and presenting some type of information (e.g., graphically, audibly, haptically, etc.) to a user by way of a user interface.

For example, communication device 608 in FIG. 6B may represent a personal computer, a CPI device, a combination thereof, or another suitable computing device configured to communicate with cochlear implant system 310 and to interface with a user. Similarly, communication device 610 in FIG. 6C may represent a mobile device such as a smartphone, a tablet device, a custom remote control configured to facilitate interaction with cochlear implant system 310, or the like. In certain examples, communication devices 608 and/or 610 may be general purpose computing devices upon which specialized software (e.g., a downloadable application ("app") or the like) has been loaded to implement component alignment presentation system 302. Communication device 608 and 610 may each include screens for presenting graphical representations, as well as audio output means (e.g., loudspeakers, headphone jacks, etc.) for presenting audio. Communication devices 608 and 610 may use such interfaces to present graphics such as graphic 612 illustrated on the screens of both communications devices, and to present audio. In some examples, communications devices 608 and/or 610 may also have additional ways of outputting information to a user, such as haptic feedback (e.g., vibrations, etc.), alert LEDs separate from the screen, and the like. These interfaces may also be used to indicate to a user the degree of alignment in any other way as may serve a particular implementation.

As used herein, a "user interface" may refer to any system, component, or other means by which information may be communicated to and/or received from a user. For example, certain user interfaces may be audiovisual user interfaces that include graphical elements (e.g., visual indicators 606, the screens of communication devices 608 and 610, etc.), audio elements (e.g., loudspeakers 604, the audio interfaces of communication devices 608 and 610), and/or other suitable elements (e.g., haptic interfaces that may cause sound processor 602 and/or communication devices 608 and/or 610 to vibrate). In other examples, user interfaces may not be so comprehensive. For instance, a graphical-only user interface may be configured to present only graphical representations of a degree of component alignment and may not present information using sound. Similarly, an audible-only user interface may be configured to present only sounds and may not include a screen to present information graphically. Regardless of what type of user interface is used to present information to a user, however, component alignment presentation system 302 may present the indication of the degree of component alignment by first detecting, based on a change in RSSI signal 504, a change in the degree of alignment of headpiece 314 with cochlear implant 316. Then, depending on the type of user interface employed in a particular implementation, component alignment presentation system 302 may represent the change in the degree of alignment of headpiece 314 with cochlear implant 316 in any of several different ways.

As one example, component alignment presentation system 302 may graphically represent the change by way of a color and/or a status-indicating graphic displayed on a graphical display upon which the user interface is presented. For instance, a graphic such as graphic 612 may be displayed as red while the degree of alignment is relatively low (e.g., while headpiece 314 is located on outer portions of region 402 in FIG. 4), as yellow (or a particular shade of yellow that may vary) as the degree of alignment increases (e.g., while headpiece 314 is located within outer portions of region 404), and as green when the degree of alignment reaches a particular level that is considered to be suitable for reliable and efficient communications (e.g., when headpiece 314 is located within region 406).

Additionally, along with using color in this or a similar way, the size, shape, and/or other qualities of a status-indicating graphic may further help indicate the degree of alignment. For instance, as shown, graphic 612 may be implemented as a status bar with various portions that are filled in or blanked out, or that is continuous without discrete portions, or the like. The status bar may grow (e.g., portions currently blanked out toward the top may be filled in) as the degree of alignment increases, and may shrink (e.g., portions currently filled in toward the bottom may be blanked out) as the degree of alignment decreases. It will be understood that a status bar illustrated by graphic 612 is only one of many examples of status-indicating graphics that could be used, and that any graphic capable of indicating relative status may also be used in various implementations. Additionally, it will be understood that visual indicators 606 of sound processor 602 may be used in a similar way as graphic 612 (e.g., changing colors, growing, shrinking, etc., to represent degree of alignment).

As another example of how component alignment presentation system 302 may represent the detected change in the degree of alignment of headpiece 314 with cochlear implant 316, component alignment presentation system 302 may audibly represent the change in the degree of alignment by way of a volume and/or a pitch of sound emitted by a loudspeaker by way of which the user interface is presented. For example, using one or both of loudspeakers 604 and/or using similar audio output means included within communication devices 608 or 610, component alignment presentation system 302 may play a sound (e.g., a continuous tone or any other sound as may serve a particular implementation) that has a certain pitch (e.g., a relatively low-frequency pitch) and/or a certain volume (e.g., a relatively low volume) when the degree of alignment is relatively low. The sound may then change to a different pitch (e.g., a higher-frequency pitch) and/or a different volume (e.g., a higher volume) as the degree of alignment increases. In other examples, the pitch and/or volume may get lower, rather than higher, as the degree of alignment increases. Alternatively or additionally, other aspects of sound may be employed (e.g., the timbre, type of sound, or other qualities may be altered) to indicate the alignment, or sound may be used in other ways as may serve a particular implementation (e.g., an artificial voice may verbally indicate the degree of alignment and whether the alignment is getting better or worse).

In certain examples, when system 300 detects (e.g., based on the change in RSSI signal 504) the change in the degree of alignment of headpiece 314 with cochlear implant 316, system 300 may determine, based on the detected change, that headpiece 314 is aligned with cochlear implant 316 to at least a threshold degree of alignment. For example, as described above, system 300 may determine that the degree of alignment is high enough for a strong, reliable, efficient link to be made between the components such that it may not be necessary for cochlear implant 316 to continue using power to generate and transmit the back telemetry signal.

When this threshold degree of alignment is detected to be reached, component alignment presentation system 302 may indicate this to the user by way of the user interface in any way as may serve a particular implementation. For example, component alignment presentation system 302 may represent the determination that headpiece 314 is aligned with cochlear implant 316 to at least the threshold degree of alignment by way of a change to at least one of a graphical representation presented on a graphical display and an audible representation presented by way of a loudspeaker. Specifically, for instance, the graphical representation may be changed from a color such as yellow to a color such as green, may begin to flash, may change shape or size, and/or may undergo any other suitable change to indicate that the threshold degree of alignment has been reached. Similarly, the audible representation may be changed from one type of sound to another, may change in pitch or volume more dramatically than it has changed previously (e.g., as headpiece 314 was moved around in search of the highest degree of alignment possible), or may undergo any other suitable change as may serve a particular implementation.

Figure 7:
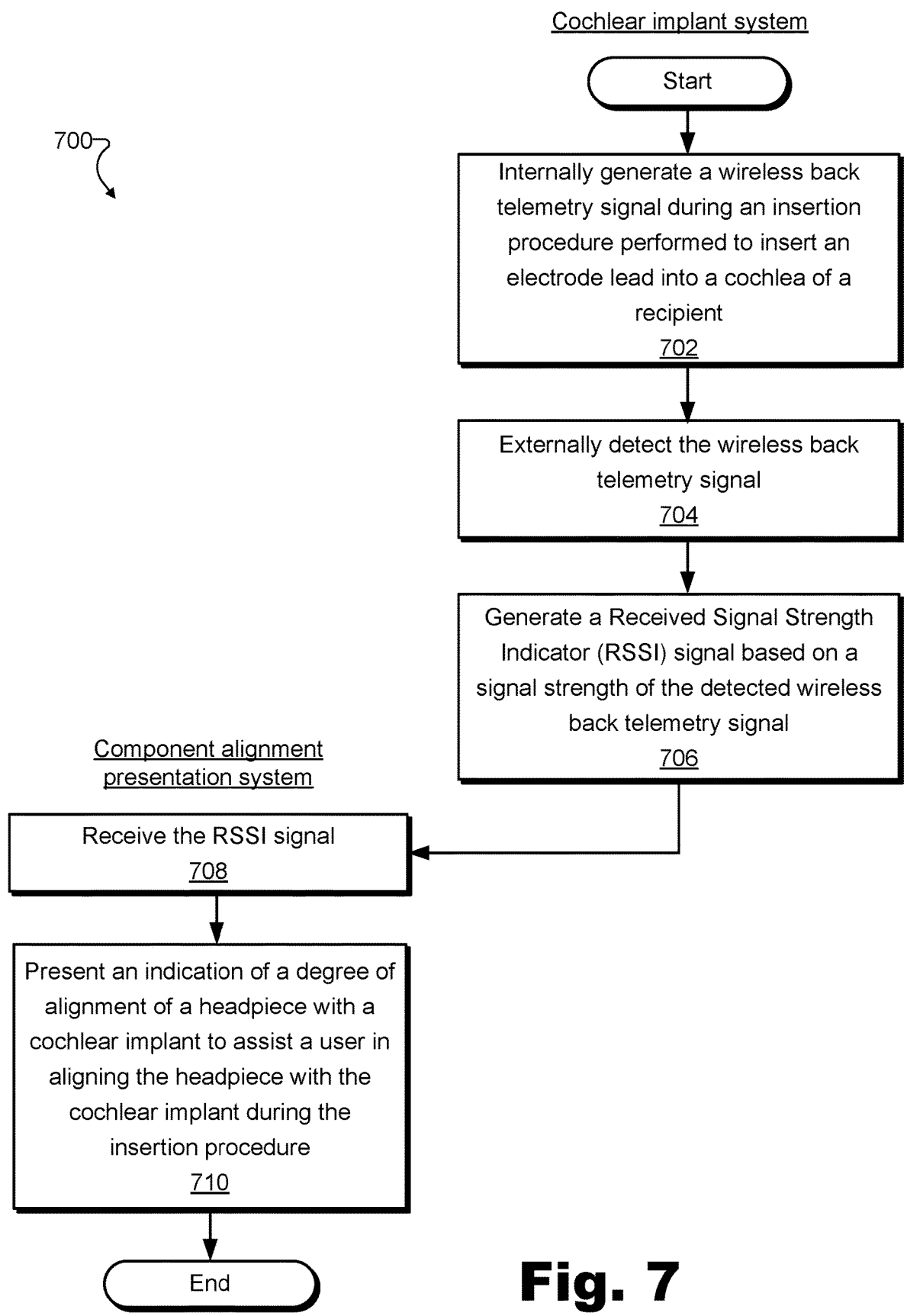
FIG. 7 illustrates an exemplary method for facilitating alignment of cochlear implant system components according to principles described herein.

FIG. 7 illustrates a method 700 for facilitating alignment of cochlear implant system components. Method 700 may be performed by a cochlear implant alignment system such as system 300 or any implementation thereof. For specifically, as illustrated, certain operations of method 700 (i.e., operations 702 through 706 on the right-hand side of FIG. 7) may be performed by a cochlear implant system (e.g., cochlear implant system 310 and/or any implementation thereof) within a cochlear implant alignment system. As further shown, other operations of method 700 (i.e., operations 708 through 710 on the left-hand side of FIG. 7) may be performed by a component alignment presentation system (e.g., component alignment presentation system 302 and/or any implementation thereof) within the cochlear implant alignment system.

While operations are shown and described in FIG. 7 as being performed by either a cochlear implant system or a component alignment presentation system, it will be understood that, as described above, the cochlear implant system and the component alignment presentation system may be integrated together into the cochlear implant alignment system in any way as may serve a particular implementation. By the same token, one or more operations illustrated as being performed by one system may be performed by the other system or by both systems in certain implementations. Additionally, while FIG. 7 illustrates exemplary operations according to one embodiment, other embodiments may omit, add to, reorder, and/or modify any of the operations shown in FIG. 7.

In operation 702, a cochlear implant included within a cochlear implant system and configured to be implanted under a skin flap of a recipient by way of an implantation procedure may generate a wireless back telemetry signal during an insertion procedure. For example, the insertion procedure may be subsequent to the implantation procedure and may be performed to insert an electrode lead permanently affixed to the cochlear implant into a cochlea of the recipient. Operation 702 may be performed in any of the ways described herein.

In operation 704, a headpiece included within the cochlear implant system and configured to operate external to the recipient may detect the wireless back telemetry signal generated by the cochlear implant in operation 702. Operation 704 may be performed in any of the ways described herein.

In operation 706, a sound processor included within the cochlear implant system may generate an RSSI signal based on a signal strength of the wireless back telemetry signal detected in operation 704. Operation 706 may be performed in any of the ways described herein.

In operation 708, the component alignment presentation system may receive the RSSI signal generated in operation 706 from the sound processor. Operation 708 may be performed in any of the ways described herein.

In operation 710, the component alignment presentation system may present an indication of a degree of alignment of the headpiece with the cochlear implant. For instance, the component alignment presentation system may present the alignment indication to a user associated with performing the insertion procedure. In some examples, the alignment indication may be presented by way of a user interface during the insertion procedure based on the RSSI signal received in operation 708. In this way, operation 710 may assist the user in aligning the headpiece with the cochlear implant while the insertion procedure is underway. Operation 710 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium (e.g., a memory, etc.) and executes the instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), erasable programmable read-only memory ("EPROM"), electrically erasable programmable read-only memory ("EEPROM"), a Flash EEPROM device, any other memory chip or cartridge, or any other tangible medium from which a computer can read.

Figure 8:
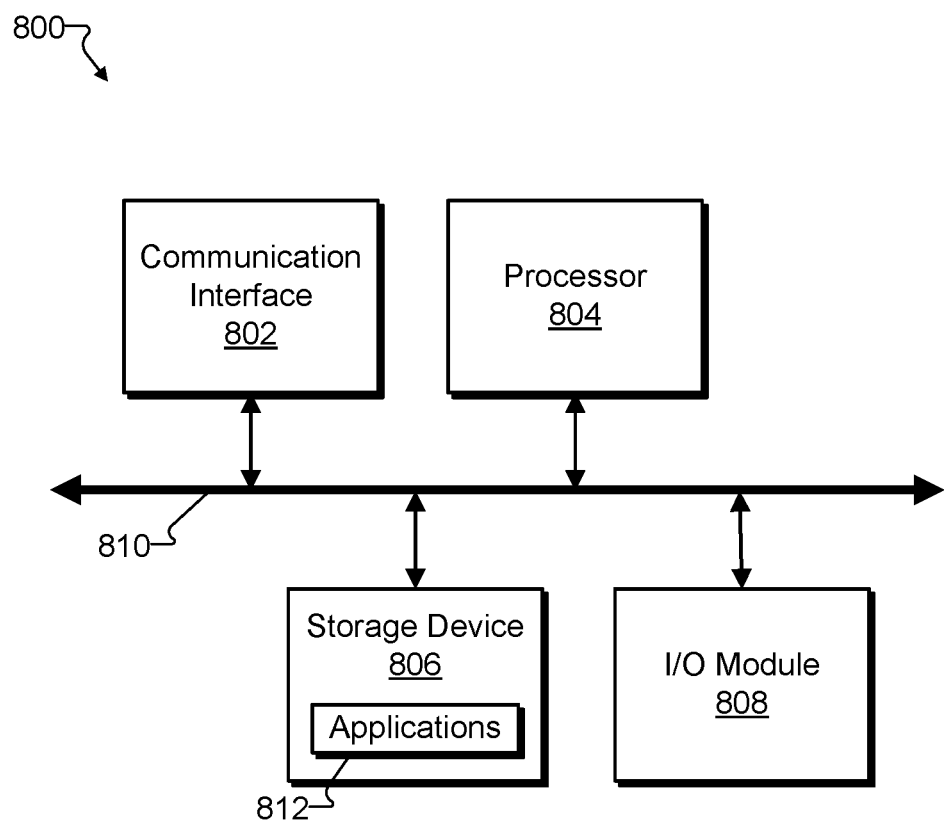
FIG. 8 illustrates an exemplary computing device according to principles described herein.

FIG. 8 illustrates an exemplary computing device 800 that may be specifically configured to perform one or more of the processes described herein. As shown in FIG. 8, computing device 800 may include a communication interface 802, a processor 804, a storage device 806, and an input/output ("I/O") module 808 communicatively connected via a communication infrastructure 810. While an exemplary computing device 800 is shown in FIG. 8, the components illustrated in FIG. 8 are not intended to be limiting. Additional or alternative components may be used in other embodiments. Components of computing device 800 shown in FIG. 8 will now be described in additional detail.

Communication interface 802 may be configured to communicate with one or more computing devices. Examples of communication interface 802 include, without limitation, a wired network interface (such as a network interface card), a wireless network interface (such as a wireless network interface card), a modem, an audio/video connection, and any other suitable interface.

Processor 804 generally represents any type or form of processing unit capable of processing data or interpreting, executing, and/or directing execution of one or more of the instructions, processes, and/or operations described herein. Processor 804 may direct execution of operations in accordance with one or more applications 812 or other computer-executable instructions such as may be stored in storage device 806 or another computer-readable medium.

Storage device 806 may include one or more data storage media, devices, or configurations and may employ any type, form, and combination of data storage media and/or device. For example, storage device 806 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 806. For example, data representative of one or more executable applications 812 configured to direct processor 804 to perform any of the operations described herein may be stored within storage device 806. In some examples, data may be arranged in one or more databases residing within storage device 806.

I/O module 808 may be configured to receive user input and provide user output and may include any hardware, firmware, software, or combination thereof supportive of input and output capabilities. For example, I/O module 808 may include hardware and/or software for capturing user input, including, but not limited to, a keyboard or keypad, a touch screen component (e.g., touch screen display), a receiver (e.g., an RF or infrared receiver), and/or one or more input buttons.

I/O module 808 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 808 is configured to provide graphical data to a display for presentation to a user. The graphical data may be representative of one or more graphical user interfaces and/or any other graphical content as may serve a particular implementation.

In some examples, any of the facilities or systems described herein may be implemented by or within one or more components of computing device 800. For example, one or more applications 812 residing within storage device 806 may be configured to direct processor 804 to perform one or more processes or functions associated with communication facility 304 or presentation facility 306 within system 300. Likewise, storage facility 308 within system 300 may be implemented by or within storage device 806.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A cochlear implant alignment system comprising:
a cochlear implant system that includes:
a cochlear implant configured to be implanted under a skin flap of a recipient and to generate a wireless back telemetry signal,
an electrode lead permanently affixed to the cochlear implant and configured to be inserted into a cochlea of the recipient,
a headpiece configured to operate external to the recipient and to detect the wireless back telemetry signal generated by the cochlear implant, and
a sound processor configured to:
generate, based on a signal strength of the detected wireless back telemetry signal, a Received Signal Strength Indicator (RSSI) signal,
determine, based on the RSSI signal, that a particular degree of alignment between the cochlear implant and the headpiece has been reached,
characterize, based on the determining that the particular degree of alignment between the cochlear implant and the headpiece has been reached, a forward telemetry signal being transmitted by the headpiece to the cochlear implant, and
determine, based on the characterizing, power levels at which intersystem communications between the cochlear implant and the headpiece are made during operation of the cochlear implant system; and
a component alignment presentation system that includes at least one physical computing device that is communicatively coupled to the sound processor and that:
receives the RSSI signal from the sound processor,
presents, based on the RSSI signal received from the sound processor, an alignment indication to assist a user in aligning the headpiece with the cochlear implant, the alignment indication visually or audibly indicating a threshold degree of alignment and a plurality of additional degrees of alignment of the headpiece with the cochlear implant, wherein the threshold degree of alignment is sufficient to achieve a communication lock between the headpiece and the cochlear implant and wherein the plurality of additional degrees of alignment are each too poor to achieve the communication lock.

2. The cochlear implant alignment system of claim 1, wherein:
the cochlear implant is configured to communicate, by way of a first communication component included within the cochlear implant, with the headpiece when the headpiece has the threshold degree of alignment with the cochlear implant;
the headpiece is configured to be disposed on an opposite side of the skin flap from the cochlear implant and to communicate, by way of a second communication component included within the headpiece, with the cochlear implant when the headpiece has the threshold degree of alignment with the cochlear implant; and
the sound processor is communicatively coupled with the headpiece and is configured to communicate with the cochlear implant by way of the headpiece.

3. The cochlear implant alignment system of claim 1, further comprising a loudspeaker configured to apply acoustic stimulation to the recipient during an insertion procedure by way of which the cochlear implant is implanted under the skin flap of the recipient, and wherein:
the sound processor is further configured, when the headpiece has the threshold degree of alignment with the cochlear implant, to:
detect an evoked response of the recipient that occurs in response to the acoustic stimulation applied to the recipient, and
provide the detected evoked response to an insertion procedure assistance system associated with the cochlear implant system and configured to assist the user in performing the insertion procedure.

4. The cochlear implant alignment system of claim 1, wherein the at least one physical computing device presents the alignment indication by way of at least one of:
a first loudspeaker included in the sound processor and configured to emit sounds to be heard by the recipient and by a user other than the recipient, or a second loudspeaker included in the sound processor and configured to emit sounds directly to the recipient to be heard by the recipient.

5. The cochlear implant alignment system of claim 1, wherein the at least one physical computing device presents the alignment indication by:
    detecting, based on a change in the RSSI signal, a change in a degree of alignment of the headpiece with the cochlear implant; and
    visually indicating the change in the degree of alignment of the headpiece with the cochlear implant by way of a plurality of visual indicators included within the sound processor.

6. The cochlear implant alignment system of claim 1, wherein the at least one physical computing device presents the alignment indication by:
    detecting, based on a change in the RSSI signal, a change in a degree of alignment of the headpiece with the cochlear implant; and
    audibly indicating the change in the degree of alignment of the headpiece with the cochlear implant by way of at least one of a volume or a pitch of sound emitted by a loudspeaker included within the sound processor.

7. The cochlear implant alignment system of claim 1, wherein the at least one physical computing device presents the alignment indication by:
    detecting, based on a change in the RSSI signal, a change in a degree of alignment of the headpiece with the cochlear implant;
    determining, based on the change in the degree of alignment of the headpiece with the cochlear implant, that the headpiece has the threshold degree of alignment with the cochlear implant; and
    representing the determination that the headpiece has the threshold degree of alignment with the cochlear implant by way of a change to at least one of a visual indicator included within the sound processor or an audible representation presented by way of a loudspeaker included within the sound processor.

8. The cochlear implant alignment system of claim 1, wherein the headpiece is further configured to wirelessly transmit the forward telemetry signal to the cochlear implant concurrently with the detection of the back telemetry signal generated by the cochlear implant, the forward telemetry signal transmitted at a different frequency than the detected back telemetry signal and including data and power based upon which the cochlear implant operates.

9. The cochlear implant alignment system of claim 1, wherein the signal strength of the detected back telemetry signal is a fixed signal strength.

10. The cochlear implant alignment system of claim 1, wherein the sound processor is configured to generate the RSSI signal as a digital signal by performing an analog-to-digital conversion of an analog signal representative of the signal strength of the detected back telemetry signal.

11. The cochlear implant alignment system of claim 1, wherein the sound processor is configured to visually indicate the threshold degree of alignment and the plurality of additional degrees of alignment by way of a plurality of visual indicators implemented within the sound processor.

12. A cochlear implant alignment system comprising:
    an insertion procedure assistance system configured to assist a user in performing an insertion procedure based on an evoked response of a recipient, the evoked response occurring in response to acoustic stimulation applied to the recipient during the insertion procedure;
    a cochlear implant system that includes:
        a cochlear implant configured to be implanted, by way of an implantation procedure prior to the insertion procedure, under a skin flap of a recipient and to generate, by way of a first coil included within the cochlear implant, a wireless back telemetry signal during the insertion procedure,
        an electrode lead permanently affixed to the cochlear implant and configured to be inserted, by way of the insertion procedure, into a cochlea of the recipient,
        a headpiece configured to operate external to the recipient and to detect, by way of a second coil included within the headpiece, the wireless back telemetry signal generated by the cochlear implant, and
        a sound processor configured to:
            communicate with the cochlear implant and provide power to the cochlear implant by way of the headpiece,
            generate, based on a signal strength of the detected wireless back telemetry signal, a Received Signal Strength Indicator (RSSI) signal,
            determine, based on the RSSI signal, that a particular degree of alignment between the cochlear implant and the headpiece has been reached,
            characterize, based on the determining that the particular degree of alignment between the cochlear implant and the headpiece has been reached, a forward telemetry signal being transmitted by the headpiece to the cochlear implant, and
            determine, based on the characterizing, power levels at which intersystem communications between the cochlear implant and the headpiece are made during operation of the cochlear implant system,
            detect the evoked response of the recipient during the insertion procedure, and
            provide the detected evoked response to the insertion procedure assistance system;
    a loudspeaker configured to apply the acoustic stimulation to the recipient during the insertion procedure; and
    a component alignment presentation system that includes at least one physical computing device that is communicatively coupled to the sound processor and that:
        receives the RSSI signal from the sound processor,
        presents, based on the RSSI signal received from the sound processor and during the insertion procedure, an alignment indication to assist a user associated with performing the insertion procedure in aligning the headpiece with the cochlear implant while the insertion procedure is underway, the alignment indication visually or audibly indicating a threshold degree of alignment and a plurality of additional degrees of alignment of the headpiece with the cochlear implant, wherein the threshold degree of alignment is sufficient to achieve a communication lock between the headpiece and the cochlear implant and wherein the plurality of additional degrees of alignment are each too poor to achieve the communication lock.

13. The cochlear implant alignment system of claim 12, wherein the at least one physical computing device presents the alignment indication by:
    detecting, based on a change in the RSSI signal, a change in a degree of alignment of the headpiece with the cochlear implant; and
    visually indicating the change in the degree of alignment of the headpiece with the cochlear implant by way of a plurality of visual indicators included within the sound processor.

14. The cochlear implant alignment system of claim 12, wherein the at least one physical computing device presents the alignment indication by:
- detecting, based on a change in the RSSI signal, a change in a degree of alignment of the headpiece with the cochlear implant; and
- audibly indicating the change in the degree of alignment of the headpiece with the cochlear implant by way of at least one of a volume or a pitch of sound emitted by a loudspeaker included within the sound processor.

15. The cochlear implant alignment system of claim 12, wherein the at least one physical computing device presents the alignment indication by:
- detecting, based on a change in the RSSI signal, a change in a degree of alignment of the headpiece with the cochlear implant;
- determining, based on the change in the degree of alignment of the headpiece with the cochlear implant, that the headpiece has the threshold degree of alignment with the cochlear implant; and
- representing the determination that the headpiece has the threshold degree of alignment with the cochlear implant by way of a change to at least one of a visual indicator included within the sound processor or an audible representation presented by way of the loudspeaker.

* * * * *